(12) United States Patent
Pavcnik et al.

(10) Patent No.: US 7,914,567 B2
(45) Date of Patent: Mar. 29, 2011

(54) STENT TISSUE GRAFT PROSTHESIS

(75) Inventors: Dusan Pavcnik, Portland, OR (US); Clay D. Fette, Lebanon, IN (US); Jason A. Mead, Plainfield, IN (US); Joseph F. Obermiller, West Lafayette, IN (US); Fred T. Parker, Unionville, IN (US)

(73) Assignees: Oregon Health & Science University, Portland, OR (US); Cook Incorporated, Bloomington, IN (US); Cook Biotech, Inc., West Lafayaette, IN (US)

( * ) Notice: Subject to any disclaimer, the term of this patent is extended or adjusted under 35 U.S.C. 154(b) by 570 days.

(21) Appl. No.: 10/719,415

(22) Filed: Nov. 21, 2003

(65) Prior Publication Data

US 2004/0176833 A1    Sep. 9, 2004

Related U.S. Application Data (60) Provisional application No. 60/428,640, filed on Nov. 22, 2002.

(51) Int. Cl.
*A61F 2/06* (2006.01)

(52) U.S. Cl. ..................... 623/1.13; 623/1.16

(58) Field of Classification Search .......... None
See application file for complete search history.

(56) References Cited

U.S. PATENT DOCUMENTS

| | | | | |
|---|---|---|---|---|
| 5,571,173 | A | * | 11/1996 | Parodi ............... 623/1.13 |
| 5,628,788 | A | * | 5/1997 | Pinchuk ............. 623/1.2 |
| 5,865,723 | A | * | 2/1999 | Love ..................... 600/36 |
| 5,891,193 | A | * | 4/1999 | Robinson et al. ...... 128/898 |
| 5,916,264 | A | | 6/1999 | Von Oepen et al. |
| 6,214,039 | B1 | * | 4/2001 | Banas et al. ......... 623/1.13 |
| 6,334,868 | B1 | | 1/2002 | Ham |
| 6,358,284 | B1 | * | 3/2002 | Fearnot et al. ...... 623/23.72 |

FOREIGN PATENT DOCUMENTS

| | | |
|---|---|---|
| WO | WO97/24081 | 7/1997 |
| WO | WO 01/82836 A2 | 11/2001 |
| WO | WO 02/089707 A1 | 11/2002 |

OTHER PUBLICATIONS

International Preliminary Examination Report for PCT Application No. PCT/US0337365 dated Feb. 25, 2005.
International Search Report for PCT Application No. PCT/US0337365 dated Feb. 25, 2005.

\* cited by examiner

*Primary Examiner* — Corrine M McDermott
*Assistant Examiner* — Christopher D Prone
(74) *Attorney, Agent, or Firm* — Brinks Hofer Gilson & Lione (57) ABSTRACT

A stent tissue graft prosthesis (20) for repairing, excluding and/or reinforcing a vessel, duct and the like in a patient. The prosthesis includes an inner expandable stent (21) of which a tissue graft (24) and preferably a multilayered tissue construct (33) is disposed thereon for application to the host tissue of a vessel, duct and the like. The tissue construct includes an extracellular matrix material (36) such as small intestine submucosa (37) for remodeling the host tissue into the prosthesis. The prosthesis further includes an outer tubular member (25) such as an outer expandable stent (44) for retaining the tissue graft on the inner stent. The ends of the inner and outer stents are coincident with or extend beyond the ends of the tissue graft to prevent eversion or fold back of the tissue graft during withdrawal of a delivery catheter in a placement procedure.

21 Claims, 9 Drawing Sheets

STENT TISSUE GRAFT PROSTHESIS

CROSS-REFERENCE TO RELATED APPLICATIONS

This application claims priority of provisional application Ser. No. 60/428,640, filed Nov. 22, 2002.

TECHNICAL FIELD

This invention relates generally to medical devices and, in particular, to a stent and tissue graft prosthesis and to a delivery system for delivering the prosthesis to an implantation site such as, for example, an aneurysm in the vascular system of a human or animal patient.

BACKGROUND OF THE INVENTION

As background, submucosa tissues have been suggested and used as tissue graft materials. For example, U.S. Pat. No. 2,127,903 to Bowen describes various tubes for surgical purposes which may be constructed of the submucosa layer of animal intestinal tissue. Bowen teaches constructing the tubes using a multiplicity of tissue ribbons or threads which are wound over a tubular form and dried.

U.S. Pat. No. 3,562,820 to Braun describes the use of submucosa or serosa tissues to form prosthesis devices. In one embodiment, Braun describes preparing a tubular prosthesis by drawing submucosa over a tube and drying the tissue. Braun teaches that this procedure may be repeated until the desired wall thickness is obtained.

U.S. Pat. No. 4,956,178 to Badylak et al. teaches tissue graft compositions comprising the tunica submucosa of a segment of small intestine of a warm-blooded invertebrate, wherein the tunica submucosa is delaminated from the tunica muscular and at least the lumenal portion of the tunica mucosa. Badylak et al. teaches creating tubular constructs by manipulating a sheet of the tissue graft composition to define a cylinder and suturing or otherwise securing the tissue longitudinally.

U.S. Pat. No. 6,358,284 to Fearnot et al. describes the preparation of a tubular graft from a purified submucosa sheet, wherein a first and second opposite edge of the sheet are overlapped, and wherein layers in the overlapped region are fixed to another. The Fearnot et al. patent also discloses the potential of having a second layer of submucosa tissue overlying the first layer.

WO 01/10355 published Feb. 15, 2001 describes tubular grafts of biomaterial, such as submucosa, having lumen walls which present no seam edge traversing the entire length of the lumen, for example, wherein the lumen walls present a discontinuous seam. As described, such a device can be made using a biomaterial sheet having a plurality of extensions and a plurality of corresponding apertures. The sheet can be configured as a cylinder and the extensions extended through the apertures in the formation of the tubular medical device.

WO 01/82836 A2 published Nov. 8, 2001 describes an endovascular stent graft with a stent frame having a plurality of stents connected together with a monofilament line. A covering of collagen having an extracellular matrix (ECM), such as small intestine submucosa (SIS) is disposed through the inside and over the outside of the stent frame. The covering is affixed to the stent frame such as by being sutured onto the stent frame at the ends of the stent frame and also at the connections of the stent bodies, such as at eyelets.

U.S. Pat. No. 5,693,085 to Buirge et al. describes a stent with collagen in which the collagen is applied to the outside surface of a vascular stent.

U.S. Pat. No. 5,916,264 to Von Oepen et al. describes a stent graft having two coaxially arranged, radially expanded stents and a flexible, stretchable material layer arranged between the stents. Both stents are directly connected with one another in their end regions and the material layer is formed as a fabric band wound around an inner stent. The material layer is composed of a foil or a fabric from a body compatible material or of a biological fabric. The biological material can include an autologous or homologous vein or artery.

endoluminal exclusion of an abdominal aortic aneurysm (AAA) by Transluminal implantation of stent grafts has in selected cases become an attractive alternative to open surgical aneurysmal repair. Endoluminal exclusion has been done on an elective basis after detailed preoperative visualization and measurements have been made of the aneurysmal and adjacent arterial anatomy. Stent graft systems for both elective and emergency AAA exclusions have been typically constructed with conventional surgical synthetic materials such as DACRON or polytetrafluoroethylene (PTFE) supported by typically metallic expandable stents.

Conventionally, stent grafts placed within the vascular system include one or more stents of affixed graft material including biological materials in addition to the conventional synthetic materials. As previously suggested, these biological materials can include tissue which is affixed to one or more longitudinally positioned stents using, for example, sutures which are affixed to folded over tissue at the ends of the stents and similarly along the lengths of the stents. As suggested by the Von Oepen patent, stents can be used to sandwich a stretchable material layer arranged longitudinally between the two stents. However, the stents are directly connected with one another at their end regions making the end regions significantly more rigid thereat than the intermediate portion therebetween. Abrupt transitions between the stented and unstented portions can cause significant trauma and undesirable intimal hyperplasia with consequent narrowing of the vessel. This consequence is typically referred to as "edge effect." Attachment sutures or other attachment configurations allow for a leakage of blood through the covering material, thus producing undesirable and/or life-threatening endoleaks. Furthermore, simply covering a stent with a layer of tissue without any attachment thereto allows for the tissue material to be pulled back or everted over itself when a delivery catheter is pulled back over the stent graft at the implantation site. This eversion creates a significant problem in that the aneurysm is no longer excluded and in that the stent graft with its everted tissue material presents a significant problem in its removal.

SUMMARY OF THE INVENTION

The foregoing problems are solved and a technical advance is achieved in an illustrative embodiment of a stent and tissue graft prosthesis in which a tissue graft is disposed on a first or inner expandable stent and an outer tubular member such as a second or outer expandable stent is disposed over the tissue graft and around the first expandable stent for retaining advantageously the tissue graft disposed on the inner stent. As a consequence, holes through the tissue graft are advantageously minimized, if not eliminated, and the probability of endoleaks are significantly lessened. In this preferred illustrative embodiment, the ends of the inner and outer stent along with that of the tissue graft are advantageously aligned to coincide with each other. This alignment further advantageously allows host tissue coming in contact with the tissue graft to remodel and become incorporated into the prosthesis when the tissue graft includes, for example, an extracellular matrix material (ECM) such as small intestine submucosa.

Other embodiments of the present invention include extending the inner expandable stent beyond the end of the tissue graft. However, the outer tubular member is still positioned at least entirely over the tissue graft or extends beyond the ends of the tissue graft so as to advantageously prevent undesirable eversion or displacement of the tissue graft during, for example, placement of the prosthesis and, in particular, when withdrawing a delivery catheter from the prosthesis. Keeping the ends of the inner expandable stent coincident with the ends of the tissue graft prevents the tissue graft from everting or folding into the passage of the inner expandable stent. As a result, the tissue graft is prevented from narrowing the passage or lumen of the vessel and/or creating an edge, shelf, and the like for thrombus and the like to build up on or adhere to. Since the stent tissue graft prosthesis is typically placed in an arterial vessel, pulsatile blood flow can cause the eversion of the tissue graft over either end of the inner expandable stent, which is advantageously prevented when the ends of the inner expandable stent are coincident with or extend beyond the ends of the tissue graft.

The outer tubular member of the tissue stent graft prosthesis can advantageously assume one of several different configurations. In one embodiment, the tubular member includes a perforated tube or sleeve of a polymer material such as polyethyleneteraphalate (PET). The size of the perforations is advantageously selected so as to promote contact with and remodeling of the host vessel tissue therethrough. In the preferred embodiment of the stent tissue graft prosthesis, the tubular member includes a second or outer expandable stent, which can be self-expanding, balloon expandable, or a combination of both. Furthermore, the inner expandable stent can also be self-expanding, balloon expandable, or a combination of both. In the preferred embodiment, the inner and outer expandable stents each include a plurality of circumferential segments and a plurality of tie bars longitudinal interconnecting the circumferential segments. The circumferential segments advantageously include a serpentine configuration and preferably a zigzag pattern of generally straight struts interconnected by a plurality of bends. The zigzag pattern advantageously provides for a compressed stent diameter, which facilitates loading into a delivery system for delivering the prosthesis to an implantation site. When released, the zigzag pattern can typically expand six or more times its compressed diameter to bring the tissue graft between the inner and outer expandable stents in contact with the vessel wall.

The inside and outside diameters of each of the inner and outer expandable stents in a relaxed condition is selected to retain the tissue graft disposed on the inner stent and at the same time apply sufficient outward pressure to maintain the tissue graft in contact with the vessel wall without causing damage to either the tissue graft or the vessel wall. In addition, the diameters can be selected to accommodate different loading procedures and whether the tissue construct is hydrated, lyophilized or a combination of both during the loading procedure.

In a preferred embodiment, the outside diameter of the inner stent is selected to be greater than the inside diameter of the outer stent. This embodiment helps facilitate the loading of a stent and lyophilized tissue graft prosthesis into an introducer or delivery system. This is also applicable to hydrated tissue. The lyophilized tissue graft is preferably selected to have a diameter in between the dimensions of the inner and outer stents and is thus advantageously disposed and retained on the inner stent and in direct contact with the vessel wall.

In another embodiment using a hydrated tissue graft, the outer diameter of the inner stent is selected to be less than the inner diameter of the outer stent. Again, the tissue graft is preferably selected to have a diameter in between these two inner and outer stent dimensions. Such an embodiment provides for the loading of a hydrated tissue graft over the inner stent while providing sufficient tolerance for loading the outer stent over the hydrated tissue graft without causing injury or damage thereto. When positioned in an introducer system, there is always sufficient pressure between the inner and outer stent so as to retain the tissue graft disposed on the inner stent. Typically, it is preferred to oversize the prosthesis approximately 10% to 20%, preferably 10% to 15%, and more preferably 10% with respect to the vessel lumen diameter so as to maintain sufficient outward force on the tissue graft and stents to eliminate or minimize migration of the prosthesis in the implanted vessel. Oversizing the stent tissue graft prosthesis to more than 20% of the vessel diameter can cause trauma to the vessel wall and, in particular, migration of the stent through the vessel wall.

In a preferred and best mode embodiment, the outside diameter of the inner stent is greater than the inside diameter of the outer stent as previously described. However, a dry, laminated, tubular tissue graft construct is inserted into the outer stent, which is preferably nitinol and in a fully martensitic and expanded state. The dry construct is preferably formed by vacuum pressing the water therefrom; however, lyophilization can be utilized to remove the water as well. The inner stent, which is preferably nitinol and in a fully martensitic and compressed state, is inserted into the dry tubular construct with the outer stent therearound. The combination tissue graft construct with the stents therearound is rehydrated and loaded onto the delivery system cannula. The rehydrated construct is compressed, frozen and loaded into the sheath of the delivery system. While frozen or at least still rehydrated, the tissue graft in the delivery system is freeze-dried or evaporative cooled. This tissue graft construct and stent combination is advantageously loaded into a delivery system without tearing the tissue or causing pin holes therein, which can occur when simply loading a lyophilzed or dried tissue construct into a delivery system.

In yet another embodiment, the inside and outside diameters of the inner and outer expandable stents are selected to be equivalent to exert more compressive force on a hydrated tissue graft or less compressive force on a lyophilized tissue graft.

In another aspect of a preferred embodiment of the stent tissue graft prosthesis of the present invention, the tissue graft preferably includes at least one seamless tube of tissue, tissue including extracellular matrix material and more preferably a seamless tube of small intestine submucosa for advantageously remodeling host tissue coming in contact therewith. In the preferred illustrative embodiment, the tissue graft includes a multilayer tissue construct including a plurality of seamless tubes of tissue including extracellular matrix material. The construct advantageously includes at least an inner and an outer seamless tube of porcine small intestine submucosa of different nominal diameters, which is typically harvested from at least two different weight juvenile contributors. To advantageously add further strength to the multilayered construct, a sheet of tissue from mature porcine small intestine submucosa tissue will be used. Thus, one preferred construct will include an inner tube of juvenile porcine small intestine submucosal tissue. Next, at least one sheet of mature porcine small intestine submucosal tissue is advantageously wrapped around the inner seamless tube one or more times to add further strength to the construct. In addition, an outer seamless tube of juvenile porcine tissue is disposed over the wrapped sheet of mature porcine tissue. To further bind the construct together, a fibrin and/or fibrinogen glue is applied to the layers of the construct during formation thereof to further bind the layers and construct together. Another preferred method of laminating the construct together is vacuum pressing the ECM layers together. The hydrated construct is then lyophilized to further advantageously concentrate and/or compress the layers of the construct to form a rehydrated wall thickness that is less than the initial hydrated thickness of the pre-lyophilized tissue construct. This advantageously produces a tissue graft that further reduces the wall thickness of the construct and the overall thickness of the stent tissue graft prosthesis of the present invention.

To address and avoid potential pinhole leaks in juvenile porcine tissue, at least one sheet of mature porcine tissue is wrapped around a mandril to form preferably a four layer laminated tissue construct. A minimum of one mature porcine tissue sheet or layer is contemplated, but a tissue construct of six or more laminated layers of mature porcine tissue is also contemplated at the other end of the range of tissue layers. However, a construct comprising four layers of mature porcine tissue represents the preferred, best mode embodiment of the present invention.

A further advantage of the stent tissue graft prosthesis of the present invention is that the ends of the inner stent and the outer tubular member and, in particular, the outer expandable stent are preferably not affixed to one another. Although such fixation would initially appear to better contain the tissue graft therebetween, the added stiffness of the end portions of the inner stent and outer member would further traumatize the tissue immediately adjacent and extending beyond the ends of the prosthesis. Such trauma can be minimized by staggering the ends of the inner stent and outer tubular member as previously suggested; however, the tissue graft must not extend beyond the ends of the inner stent and the outer tubular member should fully cover the tissue graft so as to prevent undesirable eversion during the delivery procedure.

DETAILED DESCRIPTION

Figure 1:
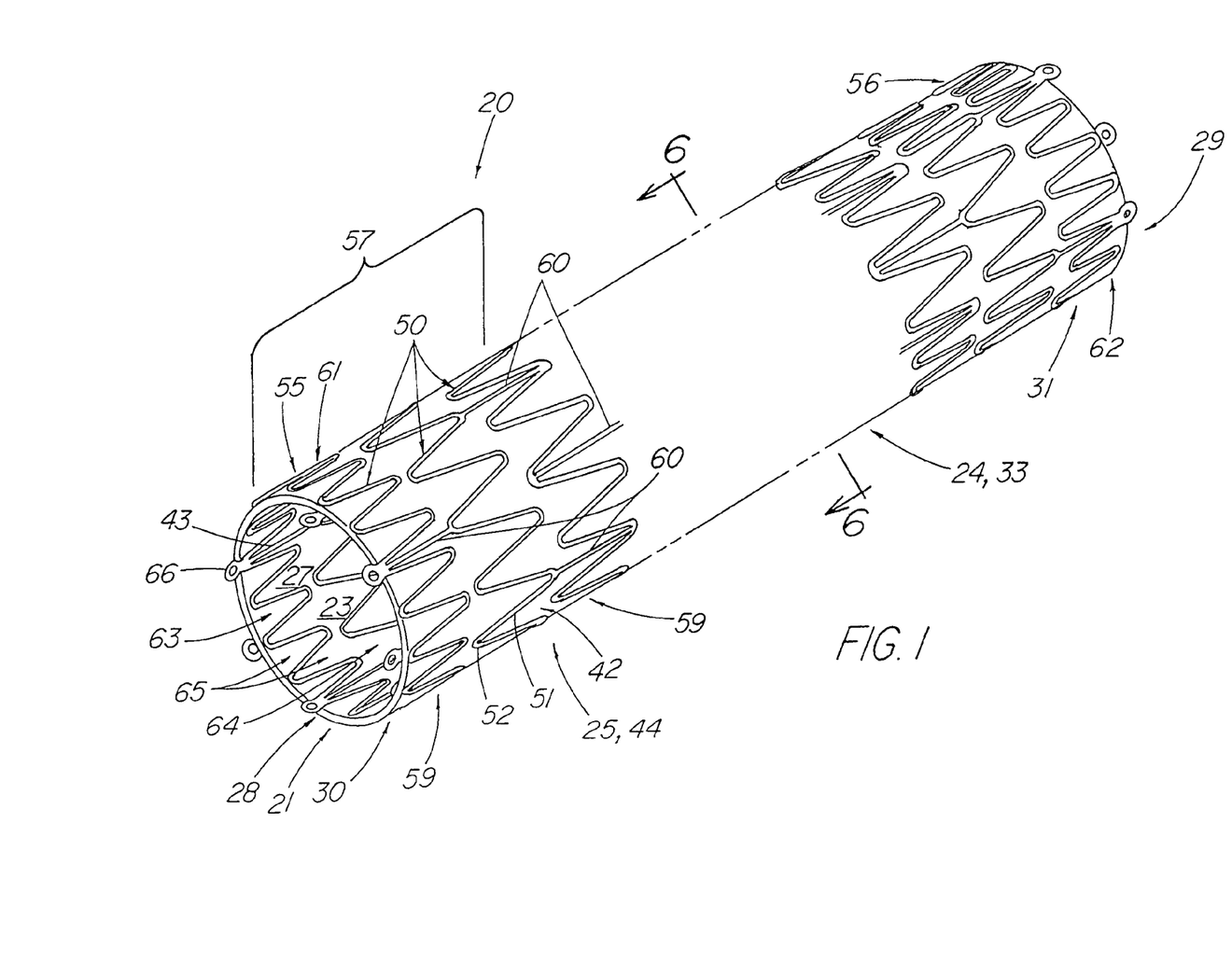
FIG. 1 depicts a pictorial view of a preferred embodiment of the stent tissue graft prosthesis of the present invention.

FIG. 1 depicts a pictorial view of a preferred illustrative embodiment of stent tissue graft prosthesis 20 of the present invention. In addition, this preferred embodiment depicts the best mode of the present invention. Stent tissue graft prosthesis 20 includes a first or inner expandable stent 21 having a passage 23 extending longitudinally therethrough, a tissue graft 24 disposed on inner stent 21 and a tubular member 25 such as a second or outer expandable stent 44 with a passage 27 extending longitudinally therethrough and disposed over the tissue graft and around the inner expandable stent so as to advantageously retain the tissue graft disposed on the first inner stent. The first or inner expandable stent has a distal inner stent end 28 and a proximal stent end 29. Similarly, tissue graft 24 has a distal graft end 30 and a proximal graft end 31. In like fashion, tubular member 25 and, in particular, outer expandable stent 44 includes distal tubular or outer stent end 55 and proximal tubular or outer stent end 56. In this preferred and best mode embodiment of the present invention, the tissue graft 24 includes a multilayered tissue construct 33 of which the distal and proximal graft ends 30 and 31 thereof are coincident longitudinally with the respective, coincidently disposed distal and proximal ends of the inner and outer expandable stents 21 and 44. The distal and proximal ends of tissue graft 24 are coincident with the respective distal and proximal ends of inner stent 21 to prevent the tissue graft from folding over or everting into passage 23 of the inner stent during pulsatile flow of blood when the prosthesis is positioned in, for example, an arterial vessel of a patient. The fold-over or eversion of the tissue graft into the passage or lumen of the inner stent can cause turbulent blood flow and can clearly create a lumen restriction for thrombus to build up on and further restrict blood flow. This can occur at either end of the prosthesis during antegrade and retrograde pulsatile blood flow. In addition, the inner expandable stent applies outward radial expansion force against the tissue graft and outer stent to keep the tissue graft in direct physical contact with the wall of a vessel when implanted therein. The direct contact of the tissue graft with that of the vessel wall facilitates remodeling of the host vessel wall cells or tissue into the tissue graft particularly when the tissue graft includes extracellular matrix material such as small intestine submucosa.

The distal and proximal tubular or outer stent ends 55 and 56 are disposed coincidently with the respective distal and proximal ends of the inner expandable stent and the tissue graft. The ends of the tubular member or outer stent are coincident with the tissue graft so as to preferably prevent eversion or fold-over of the tissue graft during withdrawal of a delivery catheter that is used to place the prosthesis at the placement site in a vessel. Should the outer tubular member or stent not be positioned over the entire length of the tissue graft, there can be sufficient adhesion between the tissue graft and delivery catheter so as to evert, fold over or pull back the tissue graft over itself and the inner stent as the delivery catheter is pulled back from the prosthesis. The outer tubular member or stent prevents such eversion, fold over or pull back of the tissue graft particularly at the ends and further maintains the uniform wall thickness of the prosthesis along its entire length.

Figure 2:
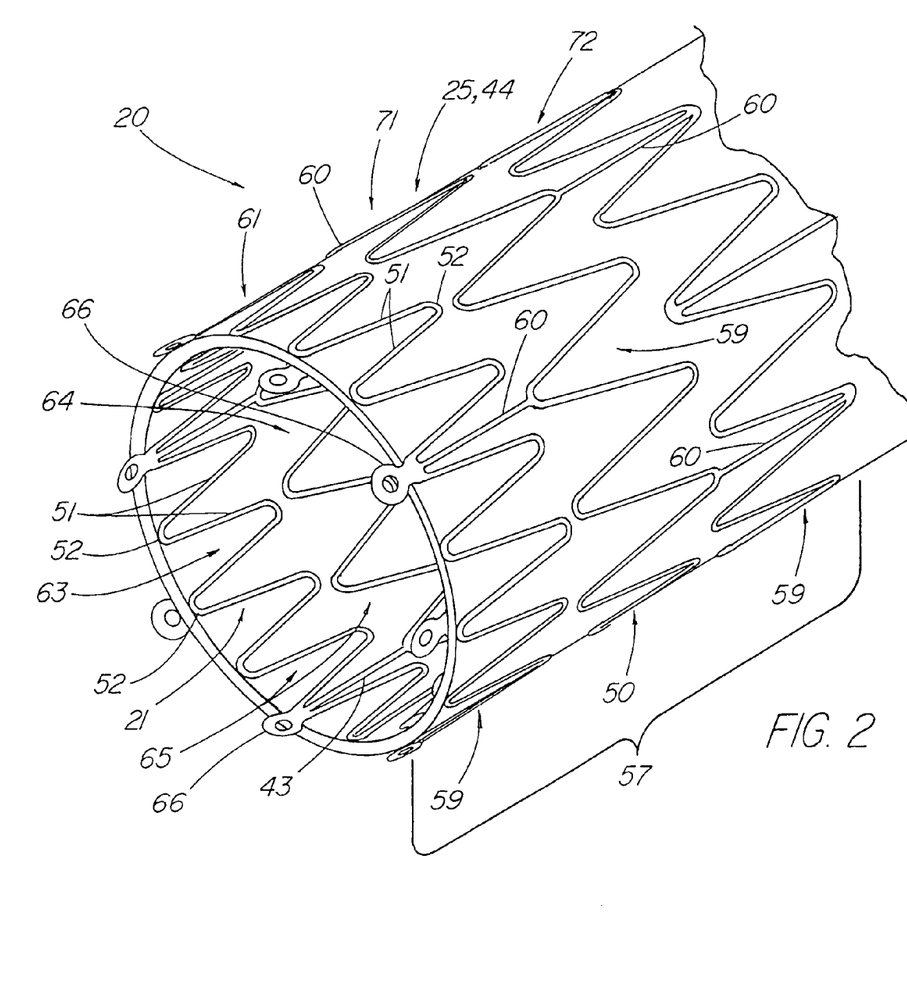
FIG. 2 depicts a partial and enlarged pictorial end view of the prosthesis of FIG. 1.

FIG. 2 depicts a partial and enlarged pictorial end view of prosthesis 20 of FIG. 1. In this enlarged end view of the prosthesis, outer tubular member 25 such as outer expandable stent 44 includes a plurality of circumferential cell segments 57 including distal end cell segment 61, flexible interconnection cell segment 71, and hoop cell segment 72 that extend longitudinally along the length of the stent. A plurality of tie bars 60 extend longitudinally along the outer stent and interconnect circumferential segments 57. A detailed description of the inner and outer stents including circumferential segments interconnected by longitudinally extending tie bars is disclosed in U.S. patent application Ser. No. 10/267,385, Publication No. US 2003-0088310 A1, filed Oct. 9, 2002, and entitled "Cannula Stent," which is incorporated by reference herein in its entirety. The flexible interconnection cell segments provide lateral flexibility for the stent, whereas the end and hoop cell segments have higher radial strength for maintaining the vessel open. However, the distal and proximal end cell segments 61 and 62 (FIG. 1) preferably exert less outward radial force so as to advantageously minimize "edge effect" trauma due to the abrupt change in force between the stented and unstented vessel wall. Each segment includes a serpentine pattern 50 of which the end and hoop cell segments include a serpentine pattern known as a zigzag or Z pattern 59.

Inner expandable stent 21 is similar to outer expandable stent 44 and includes a plurality of circumferential cell segments 65 including distal end cell segment 63, flexible interconnection cell segment 64, and hoop cell segment 42 (not shown). As previously suggested, the circumferential segments 65 and 57 of respective inner and outer expandable stents 21 and 44 each include a serpentine zigzag pattern of straight struts 51 interconnected by a plurality of bends 52. This well-known and commercially available zigzag pattern was first developed in a stent commonly known as the Gianturco Z-stent as described in U.S. Pat. No. 4,580,568 and incorporated herein by reference. The inner and outer expandable stents are also known as ZILVER® stents and commercially available from Cook Incorporated, Bloomington, Ind. One or more eyelets 66 extend from the ends of the inner and outer expandable stents and include a radiopaque material such as gold to provide radiographic visualization of the stent's position when placed in the vessel of a patient. As also previously suggested, the expandable stents can be either self-expanding, balloon expandable, or a combination of both. Self-expanding stents are typically formed from a spring-like metal such series 316L stainless steel or a shape memory alloy such as nickel titanium commonly referred to as nitinol. However, any spring-like biocompatible material is suitable so as to provide outward radial force to keep the tissue graft in contact with the vessel wall. Similarly, balloon expandable stents can be formed from stainless steel or other biocompatible materials. Either the self-expanding or balloon expandable materials can be formed from a tube or cannula or formed from a filament of spring-like material having, for example, a circular, triangular or other suitable cross-sectional shape. It is also contemplated that any expandable stent can be used with this invention and that the invention is not limited to serpentine.

Figure 3:
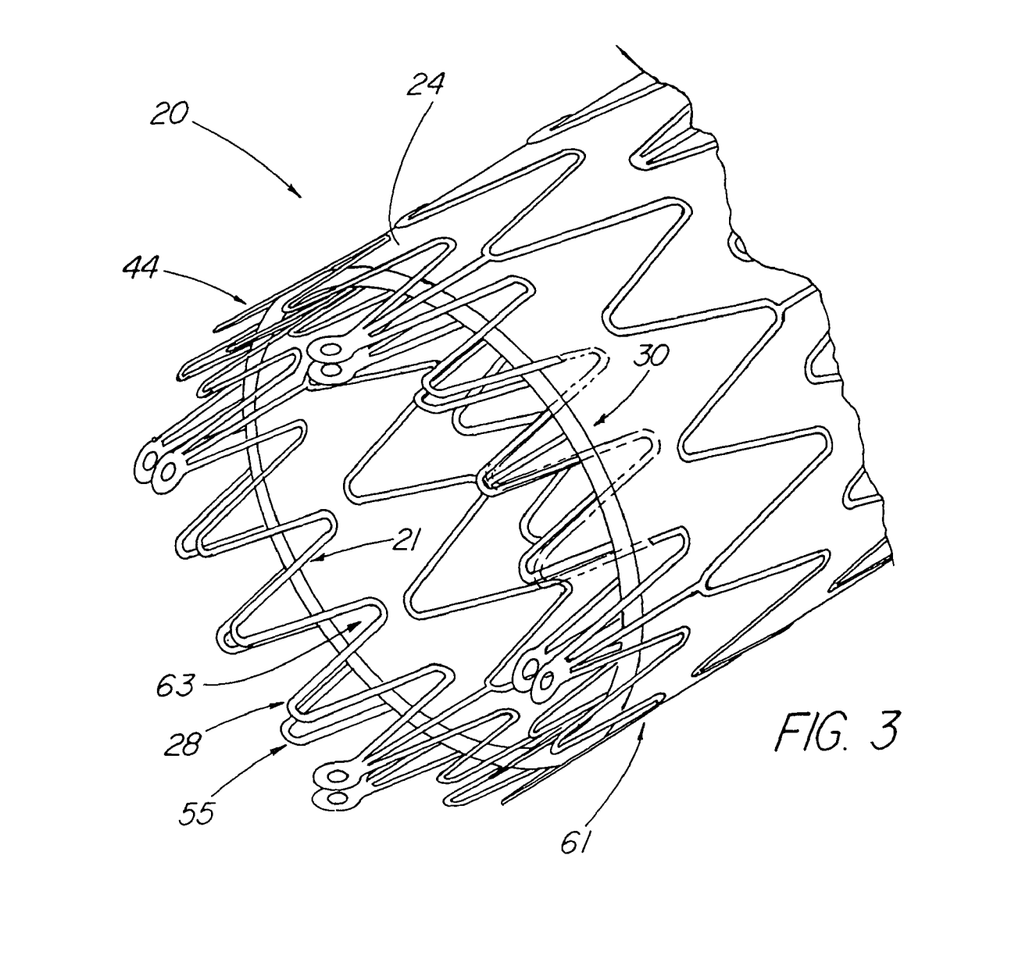
FIG. 3 depicts an enlarged and partial pictorial end view of another preferred embodiment of the prosthesis of the present invention in which the distal end of the tissue graft is longitudinally recessed from the coincident stent ends of the inner and outer stents.

FIG. 3 depicts a partial and enlarged pictorial end view zigzag, or Z stent of another preferred embodiment of prosthesis 20 of the present invention in which distal end 30 of tissue graft 24 is longitudinally recessed from distal stent end 28 of inner stent 21 that is coincident with distal stent end 55 of outer stent 44. In this embodiment, the distal end of the tissue graft is approximately 1 cm in from the coincident distal ends of the inner and outer stents. This places the distal end of the tissue graft approximately in the middle of the straight struts of outer distal end cell 61 and inner distal end cell 63. As a result, this lessens the amount of force applied at the end of the stents so as to again minimize "edge effect" at the transition of the stented and unstented portions of the vessel. In addition, the radiopaque markers and eyelets are coincident with one another on the inner and outer stent ends. However, the circumferential orientation of the eyelets and end cell struts can be rotated and staggered so as to further distribute the force applied to the captured distal end of the tissue graft.

Figure 4:
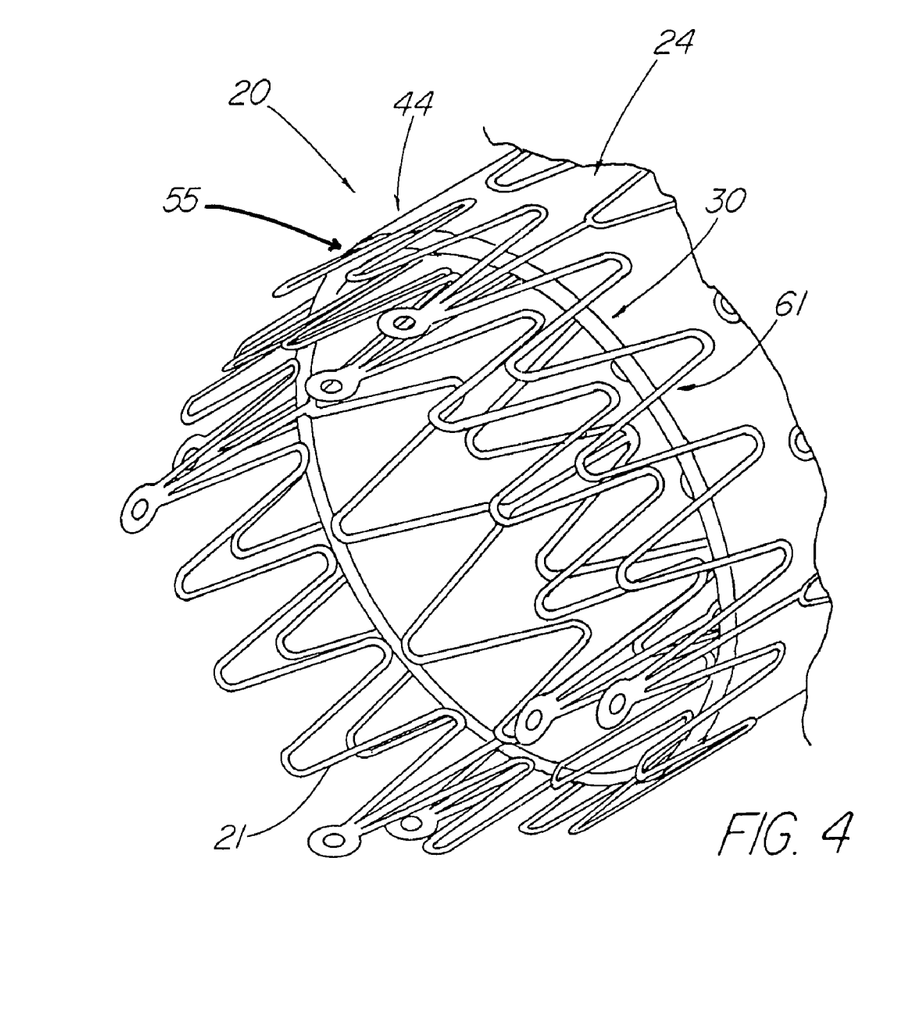
FIG. 4 depicts an enlarged and partial pictorial end view of still another preferred embodiment of the stent tissue graft prosthesis of the present invention in which the distal end of the outer stent is recessed back from the distal end of the inner expandable stent.

FIG. 4 depicts an enlarged and partial pictorial end view of still another preferred embodiment of stent 20 of the present invention in which the distal end of outer stent 44 is recessed back from the distal end of inner stent 21, and the distal end 30 of tissue graft 24 is recessed longitudinally in and from the distal ends of both inner and outer expandable stents 21 and 44. As previously detailed, the distal end 30 of the tissue graft is placed in the middle of the straight struts of the distal end cell 61. This configuration is to further distribute the radial force of the prosthesis longitudinally along the distal and proximal end portions of the prosthesis. Alternatively, the distal end 30 of tissue graft 24 can be made coincident with distal end 55 of the outer stent. However, the overriding concern is that the longitudinal force is distributed along the end portions of the prosthesis. Furthermore, the outer tubular member of the stent should completely cover the tissue graft so as to prevent an eversion of the tissue graft during withdrawal of the delivery catheter during placement in a vessel. Likewise, the end of the inner stent must be at least coincident with or extend beyond the end of the tissue graft to insure that the ends of the tissue graft do not evert or fold back into the lumen of the prosthesis and vessel and cause a restriction or resistance to blood flow.

Figure 5:
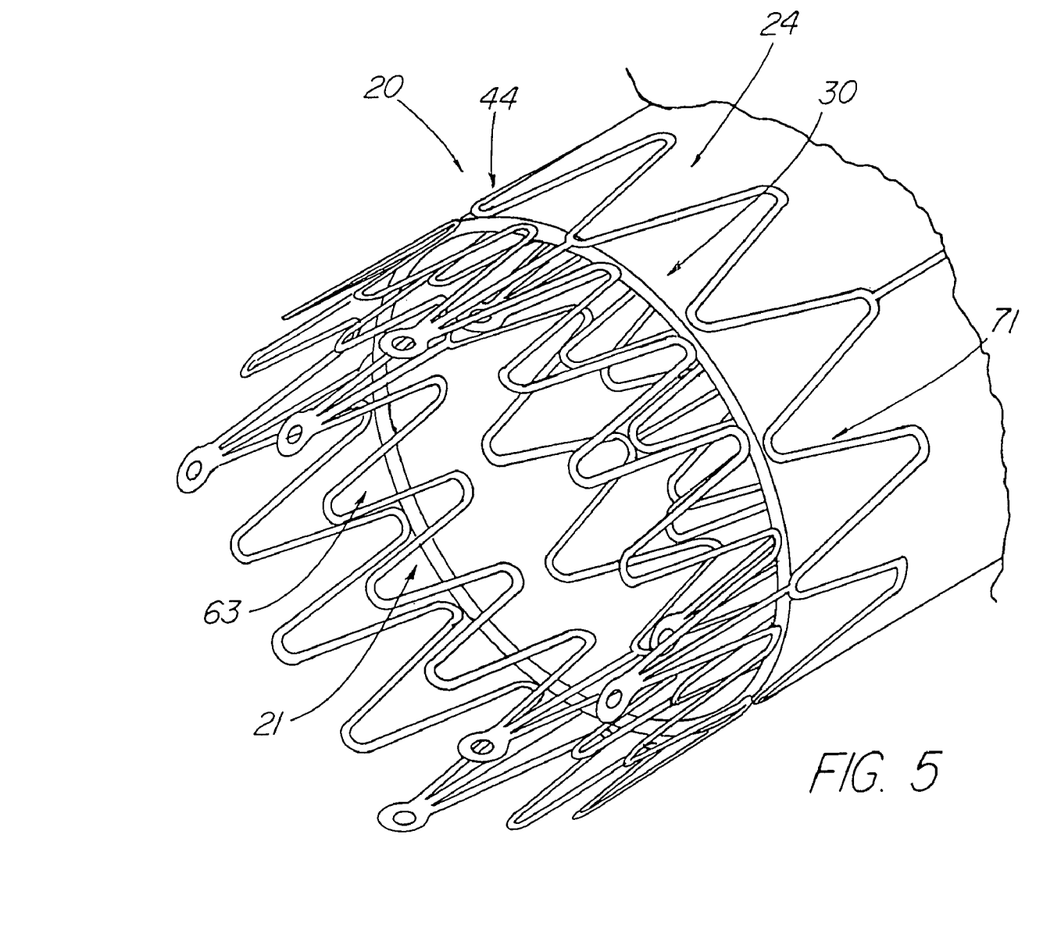
FIG. 5 depicts an enlarged and partial pictorial end view of yet another preferred embodiment of the prosthesis of the present invention in which the distal end of the inner stent is recessed back from the distal end of the outer stent and in which the distal end of the tissue graft is recessed longitudinally in and from the distal ends of both the inner and the outer expandable stents.

FIG. 5 depicts an enlarged and partial pictorial end view of yet another preferred embodiment of stent 20 of the present invention in which the distal end of inner stent 21 is recessed back from the distal end of outer stent 44, and the distal end 30 of tissue graft 24 is recessed longitudinally in and from the distal ends of both inner and outer expandable stents 21 and 44. In this embodiment, the distal end 30 of the tissue graft is placed in the middle of the straight struts of distal end cell 63 of inner stent 21. As a result, distal end 30 of the tissue graft is supported by flexible interconnection cell 71 of outer stent 44. This configuration is another embodiment for distributing the outward radial force of the prosthesis longitudinally along the distal and proximal end portions of the prosthesis. As with the embodiment of FIG. 4, the overriding concern is that the longitudinal force is distributed about the end portions of the prosthesis. Furthermore, the inner and outer stents should completely cover the tissue graft so as to prevent eversion of the tissue graft either into the prosthesis or during withdrawal of the delivery sheath during placement in the vessel.

Figure 6:
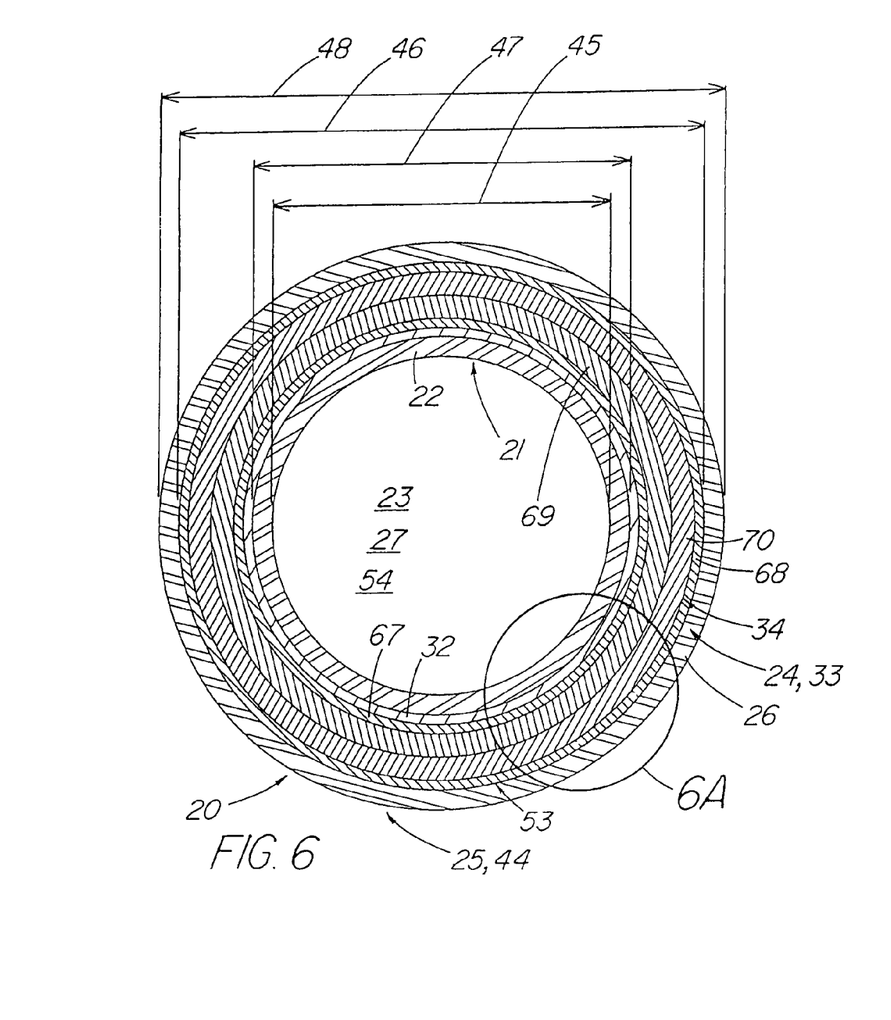
FIG. 6 depicts an enlarged and transverse cross-sectional view of the prosthesis of FIG. 1 taken along the line 6-6.
Figure 6A:
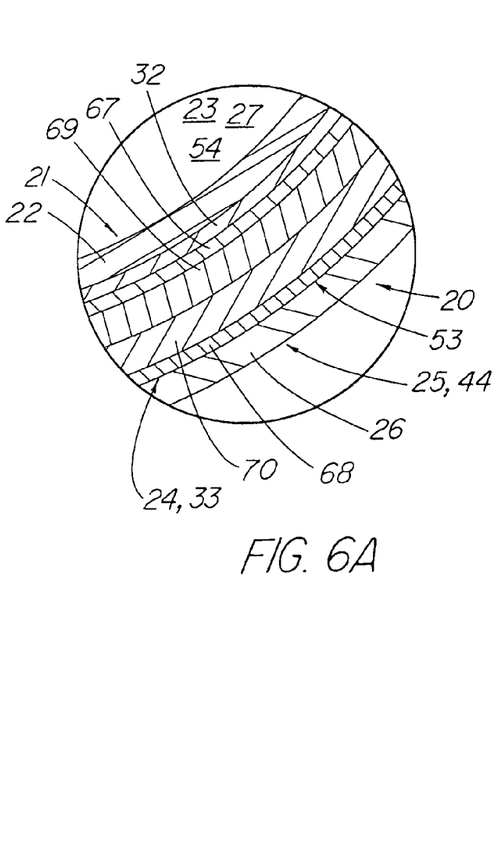

FIG. 6 depicts an enlarged and transverse cross-sectional view of prosthesis 20 of FIG. 1 taken along the line 6-6. The innermost ring depicts inner expandable stent 21 with tubular wall 22 having, for example, a wall thickness of approximately 215 microns and passage 23 extending longitudinally therethrough. The outermost ring represents tubular member 25 and, in particular, outer expandable stent 44 with tubular wall 26 having a thickness of approximately 215 microns and passage 27 extending longitudinally therethrough. As previously suggested, tubular member 25 can be a flexible tube of polymer material such as PET with perforations therein for allowing the tissue graft to contact a vessel wall. Disposed or sandwiched between inner and outer stents 21 and 44 is tissue graft 24 and, in particular, multilayered tissue construct 33. Construct 33 has a wall 53 with a thickness of approximately 500-600 microns depending on the number of layers thereof and passage 54 extending longitudinally therethrough. In this embodiment, the multilayered tissue construct includes five layers of tissue each having extracellular matrix material. The construct also includes at least one innermost seamless tube of tissue 32 of, for example, juvenile porcine small intestine submucosa (SIS). Since the juvenile small intestine submucosa does not have the density and strength of mature small intestine submucosa, a plurality of seamless tubes of juvenile SIS tissue of different diameters is contemplated.

In a preferred embodiment of the tissue construct, a first or inner most seamless tube of juvenile SIS tissue 32, a second or intermediate seamless tube of juvenile SIS tissue 67 and an outermost seamless tube of SIS tissue 68 constitute a plurality of seamless tubes of tissue 34 that would typically have a wall thickness equivalent to that of one layer of mature porcine SIS tissue. By way of example, each seamless tube of SIS tissue 32, 67, and 68 has an average thickness of approximately 100 microns and ranges in thickness from 80 to 125 microns. The thickness of a sheet of mature porcine SIS tissue material has an average thickness of approximately 250 microns and ranges in thickness from 200 to 300 microns. Thus, a tissue construct comprising three seamless tubes of juvenile porcine SIS tissue should have more than sufficient strength to withstand nominal blood pressures of typically 120 mm of mercury. This embodiment including a lyophilized three-layer tissue construct is relatively easy to load into a delivery system. However, assembly and loading of the prosthesis 20 using inner and outer stents of various diameters and a lyophilized tissue construct of three tubes of juvenile porcine SIS tissue can cause pin holes or tears in the tissue construct unless extra care and special attention is given during the assembly and loading process. However, a vacuum pressed method of assembly can also be used on this, as well as other constructs of the ECM construct, to minimize, if not eliminate, pinholes or tears during prosthesis assembly.

Accordingly, to provide further strength to the tissue construct and minimize, if not eliminate, fluid leaks, tissue construct 33 of the embodiment of FIG. 6 further includes two layers 69 and 70 of mature tissue graft material such as mature porcine small intestine submucosa which also includes extracellular matrix material. This extracellular matrix material facilitates remodeling of tissue coming in contact therewith such as the endothelial cells of a blood vessel. As a result, this five-layer tissue graft construct provides more than sufficient strength and durability to exclude, for example, an aneurysm in a blood vessel wall. Alternatively, a lyophilized multilayered tissue construct of four or five seamless tubes of juvenile porcine SIS is also contemplated to withstand damage during the loading process into a delivery catheter. In addition, inner and outer seamless tubes of juvenile SIS tissue and two layers of mature porcine SIS tissue is further contemplated for use in the prosthesis of the present invention. A detailed description of a multilayered tissue construct is disclosed in U.S. Provisional Application Ser. No. 60/408,914, filed Sep. 6, 2002, entitled "Tissue Graft Prosthesis Devices Containing Juvenile or Small Diameter Submucosa," also filed as PCT International Serial No. PCT/US03/27695, filed Sep. 4, 2003, which are incorporated by reference herein in its entirety. SIS tissue or SIS tissue constructs are commercially available from Cook Biotech, West Lafayette, Ind.

In addition, a description of a preferred extracelluar matrix material such as small intestine submucosa is described in U.S. Pat. No. 6,206,931 B1, entitled "Graft Prosthesis Materials," which is incorporated by reference herein in its entirety. The SIS material harvested from porcine for use in the present invention as described therein includes disinfecting and then stripping the various layers of the small intestine to produce an extracelluar matrix SIS material that has extremely low endotoxin levels. Tissue construct 33 is formed per the No. 60/408,914 disclosure, using for example, fibrin or fibrinogen glue to adhere the various layers of the construct together. In addition, when the construct is lyophilized, a construct typically having an initial hydrated wall thickness of approximately 800 microns reduces in thickness when re-hydrated to a thickness of approximately 500-600 microns.

Figure 7:
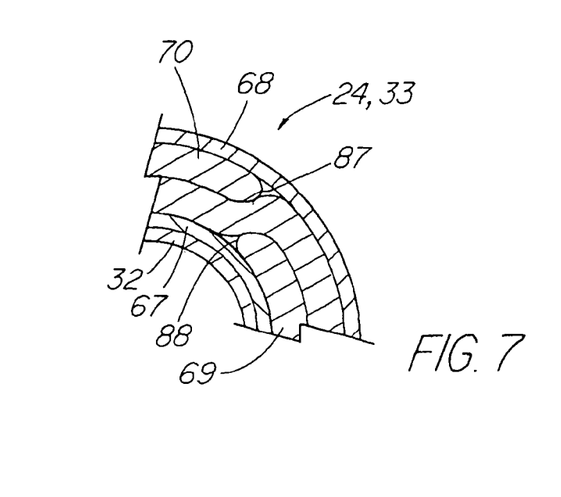
FIG. 7 depicts an enlarged and transverse cross-sectional view of a segment of the tissue graft and, in particular, the multilayered tissue construct of FIG. 6.

FIG. 7 depicts an enlarged and transverse cross-sectional view of a segment of tissue graft 24 and, in particular, multilayered tissue construct 33 of FIG. 6. This cross-sectional view of the tissue construct illustrates how the inner edge 88 of first mature tissue layer 69 is positioned with respect to outer edge 87 of second mature tissue layer 70. As depicted, inner edge 88 is one edge of a sheet of mature SIS tissue which is positioned longitudinally along the length of the construct over seamless tubes of juvenile SIS tissue 32 and 67. The sheet of mature SIS tissue is then wrapped twice around the circumference of the seamless tubes 32 and 67. Longitudinally extending outer edge 87 of the same sheet of mature SIS tissue is then positioned to abut a line extending from the center of the tubular construct that also abuts inner edge 88 of first mature SIS layer 69. As a result, a single layer of the mature tissue separates the inner and outer edge of the mature tissue sheet. To maintain the position of the sheet of the mature SIS tissue, fibrin or fibrinogen glue is applied to the surfaces of the sheet. After the mature sheet of SIS tissue is wrapped around as two layers, the outermost seamless tube of juvenile SIS tissue 68 is positioned over the wrapped sheet of mature SIS tissue.

In a best mode embodiment, one or more hydrated sheets of mature SIS tissue are wrapped around a mandrel to form a laminated construct with preferably four layers of the tissue sheet. The number of hydrated sheets is dependent on the size and, in particular, the circumference of the construct. The SIS tube is manufactured as follows: Sow weight SIS is obtained in hydrated form. This material is laid down with the longitudinal axis aligned horizontally. A rigid rod or mandrel is then placed onto the SIS at the top edge. The top edge of the SIS is then carefully pulled over onto the rigid mandrel and made as smooth and straight as possible. The material is then rolled onto the mandrel in overlapping fashion until the desired number of layers is obtained. Multiple pieces of SIS can be used to obtain the desired number or layers or thickness of material. After the material has been rolled onto the mandrel, this system (mandrel plus SIS) is placed into a commercially available vacuum pressing apparatus. One such vacuum pressing apparatus is commercially available from Zip-Vac East, Incorporated, Kennesaw, Ga. The vacuum pressing apparatus is a flexible chamber that has a vacuum drawn on it, which pulls the flexible boundaries of the chamber onto and around the mandrel/SIS. Due to the vacuum, the water is removed from the SIS, while the sides press against and around the SIS. This results in a dry, well-laminated tube of SIS material. The SIS tube is then removed from the mandrel, and the edges are trimmed to the desired length.

Further processing is required to manufacture an abdominal aortic aneurysm (AAA) stent-graft. The dry SIS tube is inserted into the desired diameter ZILVER (or other design) stent. Another stent is then deployed inside of the SIS tube. Resultingly, there is a stent on the inside, a dry SIS tube, and a stent on the outside. This construct is then rehydrated in high purity water for at least 10 minutes. The now rehydrated construct (stent/SIS/stent) is then loaded onto a delivery system cannula. It is then compressed with uniform radial force. While still compressed, the construct is frozen. After freezing, the construct is loaded into the sheath of the delivery system. While still frozen, or at least while still rehydrated, the entire system is then freeze-dried (lyophilized or evaporative cooled). This freeze-dried system is then sent to sterilization and once sterile is ready for distribution. When assembling the tissue graft construct and stents, it is preferred to have, for example, nitinol stents in a fully martensitic state so as not to introduce stress-induced martensite in the nitinol material. This is easily accomplished by placing the stent in liquid nitrogen to cool the nitinol below its martensitic final temperature. The temperature of the stents can be raised above 0° C. but below austenite start temperature so as to load hydrated SIS laminated constructs therein or therearound.

In addition, a larger diameter tube can possibly be manufactured by using tube-form SIS material. If the desired diameter of SIS tube is similar to the diameter of the tube-form SIS material, pieces of tube-form SIS can be placed onto a rigid mandrel. Multiple pieces of tube-form material can be added until the desired number of layers or thickness of the SIS device is obtained. After all of the tube-form SIS has been placed onto the mandrel, the mandrel and SIS is vacuum pressed as described before. Other manufacturing processes after vacuum pressing are identical to that listed above. The advantage of using tube-form SIS material is that a seamless inner lumen will result.

Also, an AAA stent graft can be manufactured using only one ZILVER (or other) stent, and one tube of SIS. This system would require the SIS to be affixed to the stent, for example, by glue or suture.

Also, an AAA stent graft can be manufactured by vacuum pressing the SIS component directly onto one stent. After drying, this construct can be rehydrated and compressed, loaded, and freeze dried. It is also possible to vacuum press the SIS material between two stents, further reducing the profile of the resultant device.

Figure 8:
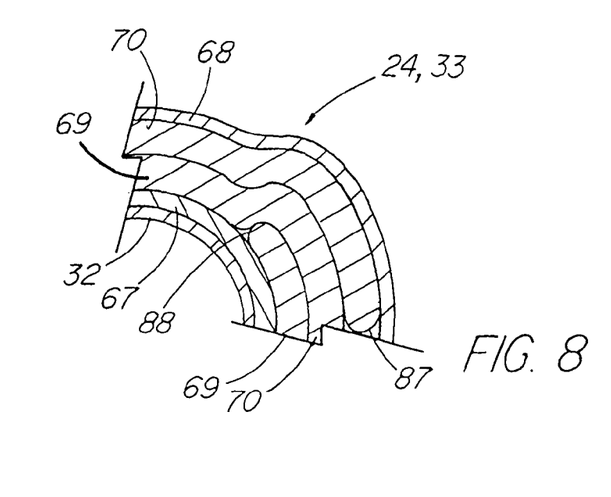
FIG. 8 depicts an enlarged and transverse cross-sectional view of another embodiment of a segment of the tissue graft and, in particular, the multilayered tissue construct of FIG. 6.

FIG. 8 depicts an enlarged and transverse cross-sectional view of another embodiment of a segment of tissue graft 24 and, in particular, multilayered tissue construct 33 of FIG. 6. In this embodiment, the single sheet of mature SIS tissue is wrapped more than twice around the first and second seamless tubes 32 and 67 of juvenile SIS tissue. In particular, the inner edge of first layer 69 is longitudinally positioned along the construct and then wrapped two and one-fourth to two and one-half times around the inner seamless tubes. This is also preferred with the previously described best mode embodiment. As a result, outer edge 87 of the single sheet of the mature SIS tissue is no longer radially aligned with inner edge 88 of the sheet. However, the additional one quarter to one-half wrap of the single sheet provides a third layer to provide additional strength over inner edge 88 of the sheet of tissue. This clearly provides a minimum of two layers of mature tissue over the inner edge of the sheet. Again, fibrin or fibrinogen glue can be applied to the sheet to help position the wrapping of the mature SIS sheet around the inner seamless tubes. Outermost seamless tube 68 is then positioned over the wrapped mature SIS tissue sheet. This outermost seamless tube keeps the wrapped sheet of mature SIS tissue in place.

Returning to FIG. 6, inner expandable stent 21 has an inside diameter 45 and outside diameter 47. Similarly, outer expandable stent 44 has an inside diameter 46 and an outside diameter 48. By way of example, prosthesis 20 can be approximately 80 mm in overall length with a nominal inside diameter of approximately 9.0 to 9.2 mm. Depending on how the prosthesis 20 is assembled and loaded into a delivery system, the diameters of the inner and outer stent along with that of the multilayered tissue construct can be selected to provide different compressive forces for the tissue construct. In a preferred embodiment of the present invention, inner stent 21 has a nominal inside diameter of approximately 10 mm in a fully relaxed condition, whereas the nominal inside diameter of outer stent 44 is approximately 9 mm in a fully relaxed condition. In this preferred method of assembly of prosthesis 20, inner stent 21 is radially compressed and inserted into a lyophilized tubular tissue construct 33 having a nominal diameter of approximately 9.5 mm. The tissue construct is then radially compressed and inserted into outer expandable stent 44 having a nominal inside diameter of approximately 9.0 mm. The ends of the inner and outer stents along with those of the tissue construct are adjusted so as to be coincident with each other. The prosthesis is then radially compressed for loading into a delivery system. Radial compression of the prosthesis can be achieved with the use of such commercially available equipment such as the SC200MSI Stent Pre-Reduction Equipment (PTA) provided by Machine Solutions, Inc., Phoenix, Ariz. Other methods of radially compressing the prosthesis without damaging the construct are also contemplated, such as flattening the tubular tissue construct, inserting the folded construct into the outer stent, and then inserting the inner stent into the folded construct and outer stent. Thus, the construct is only compressed once for loading into the delivery system. After radial compression, the prosthesis is loaded into a delivery system.

Figure 9:
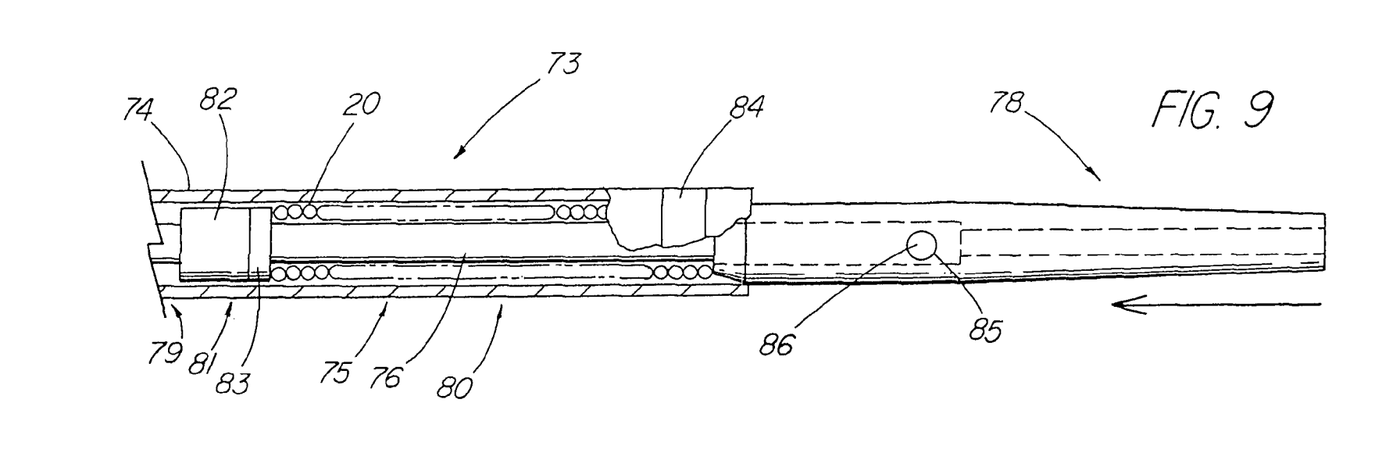
FIG. 9 depicts an enlarged and partially sectioned view of the distal end portion of the prosthesis delivery system of the present invention.

FIG. 9 depicts an enlarged and partially sectioned view of the distal end portion of prosthesis delivery system 73 of the present invention. This prosthesis delivery system is commercially available as the FLEXOR® delivery system from COOK, Inc., Bloomington, Ind. This delivery system is an over the wire system that is positioned at a placement site with the use of a well-known wire guide. A detailed description of a comparable medical device delivery system is provided in U.S. patent application Ser. No. 60/338,714, filed Nov. 29, 2001, also Publication No. US-2003-0144670-A1 and entitled "Medical Device Delivery System," which is incorporated herein by reference in its entirety. Prosthesis delivery system 73 includes delivery catheter 74 including a radiopaque marker 84 positioned about its distal end. This delivery catheter is flexible and kink resistant and is described in detail in U.S. Pat. Nos. 5,380,304 and 5,700,253, entitled "A Flexible, Kink-Resistant Introducer Sheath and Method of Manufacture," which is incorporated by reference herein in its entirety. This delivery catheter is commercially available as the FLEXOR® introducer sheath from COOK, Inc., Bloomington, Ind. The delivery catheter maintains prosthesis 20 in a radially compressed state or condition around inner member 75 of the prosthesis delivery system. Inner member 75 extends through and beyond the distal end of the delivery catheter. Inner member 75 includes a distal tip portion 78, a proximal portion 79, and an intermediate portion 80 disposed between the distal tip portion and the proximal portion. Prosthesis 20 is positioned around the recessed intermediate portion for containment thereround by delivery catheter 74. Inner member 75 includes an inner tube 76 such as a stainless steel cannula that connects to and extends proximally from the distal tip portion 78 to the proximal end of the inner member. Engagement portion 81, for example, comprising a radiopaque sleeve is positioned at the proximal end of the intermediate portion and maintained in position thereat by polymer material sleeve 82 such as commercially available heat shrink tubing. The outer diameter of sleeve 82 is heat shrunk to a size that very closely approximates the diameter of the inner lumen of the delivery catheter. An optional radiopaque marker sleeve 83 can be used to radiographically better visualize the engagement portion of the inner member. Furthermore, engagement sleeve 82 abuts the proximal end of the prosthesis and closely approximates the diameter of the inner lumen of the delivery catheter so as to prevent the prosthesis from moving longitudinally as the delivery catheter is withdrawn from the prosthesis. The use of the terms "distal" and "proximal" are referenced from typically two different reference sources. The vascular medical community will typically reference a device from the heart. Thus, "distal" with respect to an implanted medical device such as, for example, the disclosed prosthesis is farthest from the heart, while "proximal" is closest to the heart. The rest of the medical community typically references "distal" and "proximal" with respect to the attending physician as such, for example, the disclosed delivery system, which is directly opposite to that of the heart.

To load prosthesis 20 into delivery system 73, inner tube 76 of the delivery system is positioned in the lumen or longitudinal passage of prosthesis 20 that has been radially compressed. The length of inner tube 76 extends into the passage of the prosthesis without distal tip portion 78 affixed thereto. After the inner tube is positioned in the compressed prosthesis, the proximal end of the prosthesis is pushed into the lumen of delivery catheter 24 until it reaches engagement portion 81 of the inner member. After the prosthesis is fully positioned in the delivery catheter and around intermediate portion 80 of the inner member, the length of inner tube 76 is then trimmed so as to permit distal tip portion 78 to be inserted over the distal end of the inner tube as indicated by the arrow. A transverse hole or aperture 85 is positioned in the distal tip portion to allow a commercially available, biocompatible medical grade glue 86 to be inserted therein and thus cement the distal tip portion to the inner tube. As depicted, radiopaque marker 84 is positioned at the distal end of delivery catheter 74 so as to radiographically mark the distal end of the delivery catheter.

In another method of assembling prosthesis 20 and loading it into prosthesis delivery system 73, self-expanding inner stent 21 is selected to have an inside diameter of approximately 9.0 mm, and multilayered tissue construct 33 is selected to have an inside diameter of approximately 9.5 mm. The inner stent is compressed and inserted into the hydrated multilayered tissue construct and expanded to engage the hydrated construct. The inner stent and the hydrated tissue construct are then compressed to a diameter for insertion into the delivery catheter. Compressing the inner stent and hydrated tissue construct minimizes, if not eliminates, damage to the hydrated tissue construct. The compressed inner stent and hydrated tissue construct are then frozen into a compressed diameter cylindrical solid. The outer stent 48 is then compressed around the solid, and the combination loaded into the delivery catheter over the inner tube as previously described. The distal tip portion of the inner member is then attached to the inner tube. After the prosthesis has been loaded into the delivery catheter including the compressed diameter solid, the prosthesis delivery system is placed in a vacuum chamber to complete the lyophilization of the frozen tissue construct.

Figure 10:
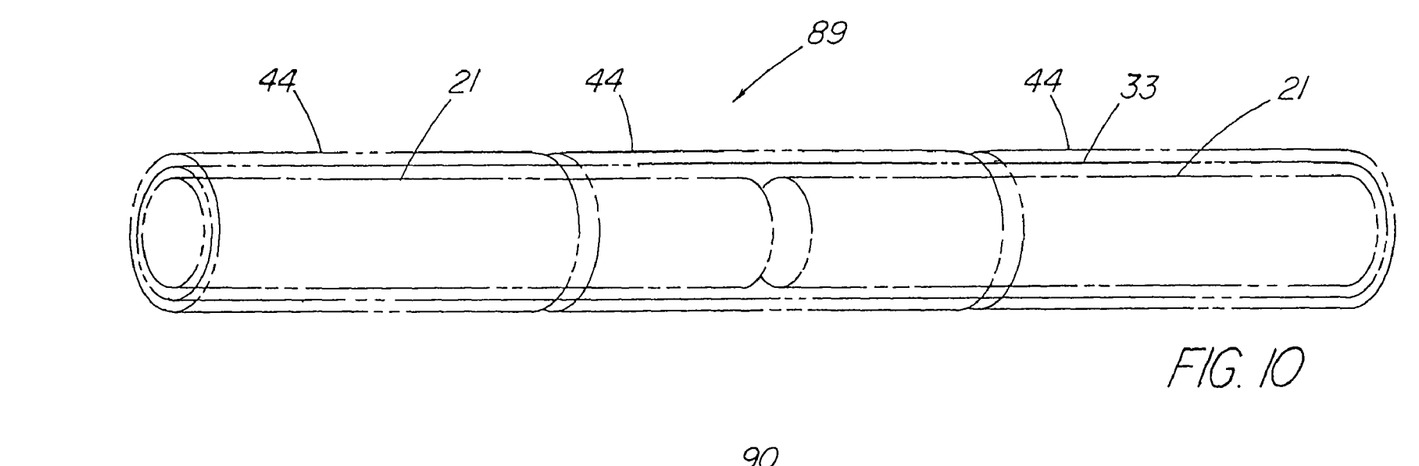
FIG. 10 depicts a pictorial view of yet another embodiment of the stent tissue graft prosthesis of the present invention.

FIG. 10 depicts a pictorial view of yet another illustrative embodiment of stent tissue graft prosthesis 89 of the present invention. In this illustrative embodiment, prosthesis 89 comprises two inner stents 21 that are positioned end to end to form a prosthesis that is the sum total length of the two inner stents. By way of example, the ZILVER stent available from COOK, Inc., Bloomington, Ind., is commercially available in lengths from 20 to 80 mm in 10 mm increments with the stent diameter ranging from 6.0 to 10.0 mm in 1.0 mm increments. Stent diameters of 12 and 14 mm are also contemplated. Accordingly, the present illustrative embodiment incorporates the use of two 80 mm long inner stents 21 positioned in a multilayered tissue construct 33 of approximately 160 mm. This multilayered tissue construct as previously described can include two or more layers of seamless tubes of juvenile SIS tissue. The construct can also include a wrapped sheet of mature SIS tissue. However, the present best mode embodiment would include a multi-layered laminate construct of mature SIS tissue only. To complete stent tissue graft prosthesis 89, three outer expandable stents 44 are positioned over the inner stents and the tissue construct such as to stagger the abutment of the two end to end inner stents. Thus, by way of example, three outer stents 44 each having a length of approximately 53 mm and a diameter of 9.0 mm could be utilized to complete the prosthesis. Alternatively, two standard length 60 mm stents in combination with a 40 mm in length stent could be used to complete the prosthesis.

Figure 11:
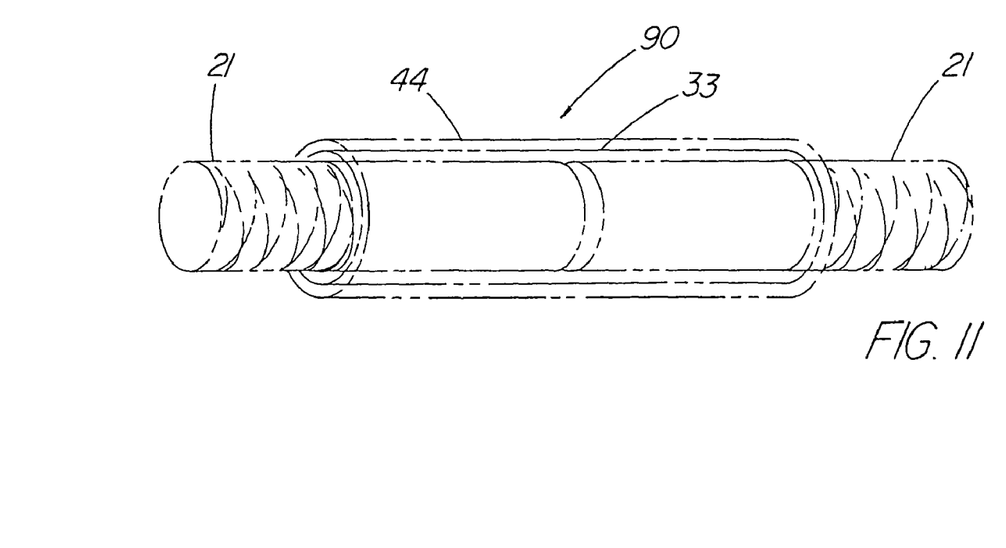
FIG. 11 depicts a pictorial view of still yet another embodiment of the tissue stent graft prosthesis of the present invention.

FIG. 11 depicts a pictorial view of still yet another illustrative embodiment of stent tissue graft prosthesis 90 of the present invention. In this illustrative embodiment, prosthesis 90 includes two end to end inner expandable stents 21 partially covered by multilayered tissue construct 33. Prosthesis 90 thus has the inner stents 21 extending beyond the ends of the tissue construct such as to allow, for example, blood flow therethrough and into branch vessels of which the prosthesis can be positioned thereacross. To retain the multilayered tissue construct on the abutting inner stents, an outer expandable stent 44 is positioned over the entire length of the tissue construct so as to prevent eversion or fold back of the tissue construct during placement in a vessel. These combinations of various length inner and outer expandable stents in combination with a multilayered tissue construct can be customized to meet a host of different anatomical sites. The ends of inner and outer stents can also be tapered to different diameters for easy adjustment to fit different aortic or iliac diameters.

Figure 12:
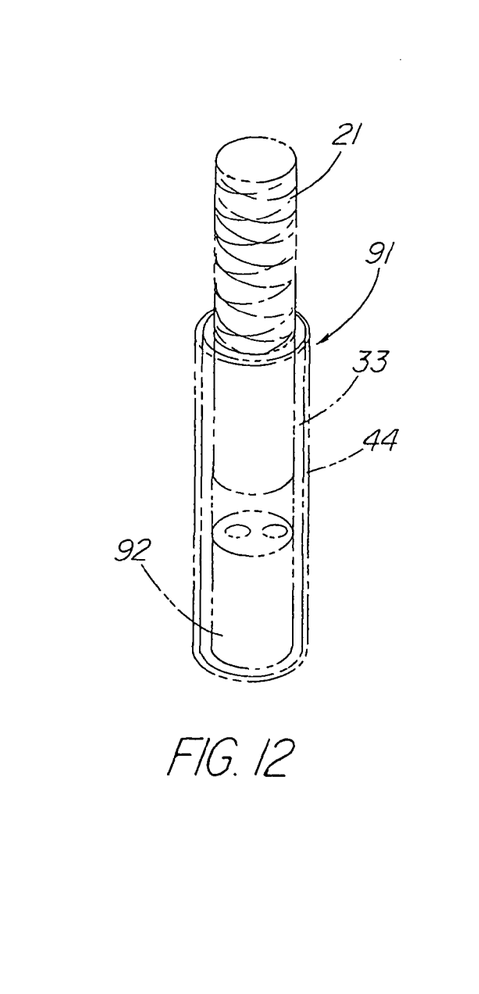
FIG. 12 depicts a pictorial view of yet still another embodiment of the stent tissue graft prosthesis of the present invention for use, by way of example, in a bifurcated vessel.

FIG. 12 depicts a pictorial view of still yet another illustrative embodiment of stent tissue graft prosthesis 91 of the present invention for use, by way of example, in a bifurcated vessel application. In this embodiment, prosthesis 91 includes an inner expandable stent 21 disposed next to drum graft occluder 92 with multilayered tissue construct 33 partially covering inner expandable stent 21 and completely covering occluder 92. Outer expandable stent 44 completely covers multilayered tissue construct 33. Drum draft occluder 92 typically comprises a tubular frame or stent with two coverings of a blood impermeable material transversely mounted on the ends of the frame. Two apertures are provided in each of the coverings to allow another prosthesis to be positioned through an aperture in each of the two coverings as will be detailed hereinafter. A detailed description of occluder 92 is provided in U.S. Pat. No. 6,325,819, which is incorporated by reference herein in its entirety. As previously suggested, inner stent 21 extends beyond the end of tissue construct 33 and outer expandable stent 44 for allowing blood flow to branch vessels when positioned at a vascular site.

Figure 13:
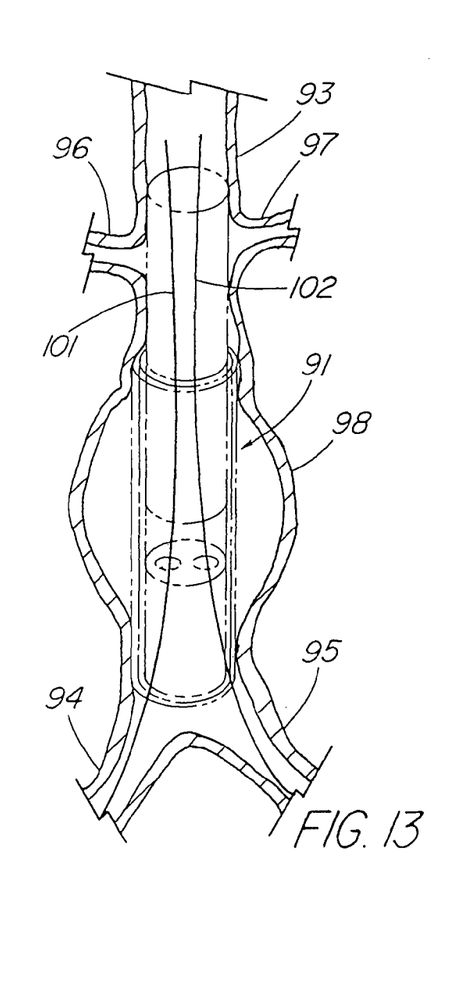
FIGS. 13 and 14 depict the endoluminal placement of the prosthesis of the present invention in an abdominal aortic aneurysm.
Figure 14:
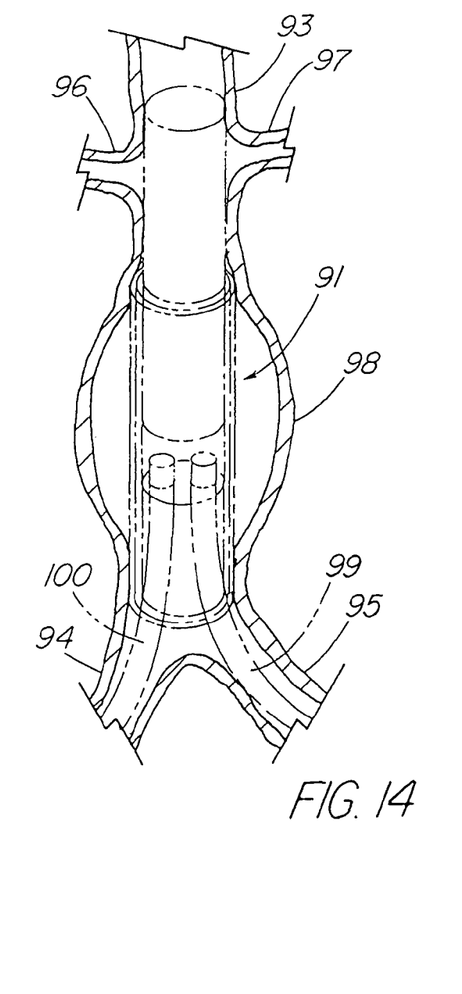

FIGS. 13 and 14 depict a cross sectional view of abdominal aortic aneurysm 98 that is positioned in aorta 93 between renal arteries 96 and 97 and iliac arteries 94 and 95. FIGS. 13 and 14 further depict the placement of bifurcated stent tissue graft prosthesis 91 in the aortic vessel and across aneurysm 98 so as to exclude the aneurysm from blood flow through the aortic vessel. Prosthesis 91 is intraluminally positioned across aneurysm 98 using a well-known minimally invasive surgically procedure via a cut-down or percutaneous insertion into the femoral arteries. In this surgical procedure, well-known and commercially available wire guides 101 and 102 are positioned through the ipsilateral and contralateral iliacs 94 and 95. In a multi-stent procedure, main body prosthesis 91 is first positioned across aneurysm 91 over a wire guide 101 via the ipsilateral iliac 94. After placement across the aneurysm, contralateral wire guide 102 is positioned through the main body prosthesis and the apertures of the occluder as shown via the contralateral iliac. As depicted in FIG. 14, an ipsilateral limb extension prosthesis 100 is inserted through the apertures of the occluder of the main body prosthesis via wire guide 101. Ipsilateral prosthesis 100 extends through the occluder of the main body prosthesis at its proximal end and extends at its distal end into ipsilateral iliac 94. Similarly, contralateral limb extension prosthesis 99 extends at its proximal end through the occluder and into the upper portion of main body prosthesis 91. At its distal end, prosthesis 99 extends into contralateral iliac 95.

Thus, it should be apparent that the stent tissue graft prosthesis of the present invention can be configured into a number of different embodiments to meet the anatomical needs of a patient by various combinations of the inner stent, multi-layered tissue construct and outer stent. Multiple inner and outer stents can be used to form combination prosthesis with portions of the stent covered and uncovered to again meet the needs of the patient. As further depicted, occluders such as previously detailed as well as a square stent adapter can be utilized to form bifurcated versions of the stent tissue graft prosthesis. By way of example, a square stent adapter is described in detail in U.S. Pat. No. 6,220,336, entitled "Multiple-Sided Intraluminal Medical Device," and published U.S. Patent Appl. No. 2001/0039450 entitled "Implantable Vascular Device," both of which are incorporated herein by reference in their entirety.

For ease of understanding, a list of elements used in the description and drawings of the present invention is included herewith. However, this element list is not to be construed to limit the present invention, but is only being provided for illustrative purposes and not to restrict the scope of the invention.

ELEMENT LIST 20 stent tissue graft prosthesis
21 first or inner expandable stent
22 tubular wall of 21
23 passage of 21
24 tissue graft
25 tubular member
26 wall of 25
27 passage of 25
28 distal stent end of 21
29 proximal stent end of 21
30 distal graft end of 24
31 proximal graft end of 24
32 at least one seamless tube of tissue of 24
33 multilayered tissue construct of 24
34 plurality of seamless tubes of tissue of 24
35 sheet of tissue of 33
36 extracellular matrix (ECM) material of 24
37 small intestine submucosa (SIS) of 24
38 first diameter tube of 34
39 second diameter tube of 34
40 self-expanding stent
41 balloon expandable stent
42 hoop cell segments of 21
43 tie bars of inner stent 21
44 second or outer expandable stent
45 first stent inside diameter
46 second stent inside diameter
47 first stent outside diameter
48 second stent outside diameter
49 perforated polymer material
50 serpentine pattern
51 plurality of straight struts
52 plurality of bends
53 construct wall of 33
54 construct passage of 33
55 distal tubular (second stent) or outer stent end of 44
56 proximal tubular (second stent) or outer stent end of 44
57 circumferential cell segments of 44
58 tie bars of 44
59 zigzag or Z pattern of 50
60 tie bars of 44
61 distal end cell segment of 44
62 proximal end cell segment of 44
63 distal end cell segment of 21
64 flex cell segment of 21
65 circumferential cell segments of 21
66 eyelets
67 second intermediate seamless tube of juvenile SIS tissue
68 outermost seamless tube of juvenile SIS tissue
69 first layer of mature SIS tissue
70 second layer of mature SIS tissue
71 flexible interconnection cell segment of 44
72 hoop cell segment of 44
73 prosthesis delivery system
74 delivery catheter
75 inner member
76 inner tube
77 not used
78 distal tip portion
79 proximal portion
80 intermediate portion
81 engagement portion
82 sleeve
83 radiopaque sleeve of 75
84 radiopaque marker of 74
85 distal tip aperture
86 glue
87 outer edge of 70
88 inner edge of 69
89 prosthesis
90 prosthesis
91 prosthesis
92 drum graft occluder
93 aorta
94 ipsilateral iliac
95 contralateral iliac
96 ipsilateral renal
97 contralateral renal
98 aneurysm 99 contralateral limb extension prosthesis
100 ipsilateral limb extension prosthesis
101 wire guide
102 wire guide It is to be understood that the above-described tissue graft prosthesis and method of assembly and use are merely illustrative embodiments of the principles of this invention. However, the invention should not be construed as limited to the particular embodiments discussed. Instead, the above-described embodiments should be regarded as illustrative rather than restricted. For example, as mentioned above, outer tubular member 24 has been described as an outer expandable stent 44. Other embodiments of the tubular member may include a polymeric tubular member in which perforations are formed therein by, for example, laser cutting and the like, for allowing host tissue to come in direct contact with the multilayered tissue construct for remodeling host tissue. This tubular member may be formed from any biocompatible material and is contemplated that such a tubular sleeve is fully within the limits of the claimed invention as follows.

What is claimed is:

1. A stent tissue graft prosthesis comprising:
    a first expandable stent having a first distal stent end and a first proximal stent end, a tubular wall and a passage extending longitudinally therethrough,
    a tissue graft having the property of eversion upon placement in a blood vessel if not supported, the tissue graft having a distal tissue graft end and a proximal tissue graft end and disposed on said first stent, but not secured to said stent, and
    a tubular member having a distal tubular member end and a proximal tubular member end, a wall and a passage extending longitudinally therethrough, said tubular member being disposed over said tissue graft and around said first stent and retaining said tissue graft disposed on said first stent solely by compressive forces, wherein the compressive forces are provided at least by an outward expansion of the first stent,
    wherein, in a pre-implantation configuration, a most distal end of the first distal stent end is at least coincident with a most distal end of the distal tissue graft end and a most proximal end of the first proximal stent end is at least coincident with a most proximal end of the proximal tissue graft end and where during implantation and post-implantation of the prosthesis, the most distal tissue graft end and the most proximal tissue graft end remain substantially in the pre-implantation configuration such that the tissue graft does not evert or fold into the passage of the first expandable stent; and
    wherein the distal and the proximal tubular member ends are substantially coincident with the respective distal and proximal first stent ends.

2. The prosthesis of claim 1, wherein said tissue graft includes at least one seamless tube of tissue.

3. The prosthesis of claim 1, wherein said tissue graft includes a multilayered tissue construct.

4. The prosthesis of claim 3, wherein said multilayered tissue construct includes a sheet of tissue.

5. The prosthesis of claim 3, wherein said multilayered tissue construct includes a plurality of laminated tissue layers ranging from two to six layers.

6. The prosthesis of claim 3, wherein said multilayered tissue construct includes a plurality of seamless tubes of juvenile porcine small intestine submucosa tissue and at least one sheet of mature porcine small intestine submucosa tissue.

7. The prosthesis of claim 1, wherein said tissue graft includes an extracellular matrix material.

8. The prosthesis of claim 7, wherein said tissue graft includes small intestine submucosa.

9. The prosthesis of claim 1, wherein said first expandable stent is a self-expanding, a balloon expandable stent or a combination self-expanding and balloon expandable stent.

10. The prosthesis of claim 1, wherein said first expandable stent has a plurality of circumferential segments and a plurality of tie bars longitudinally interconnecting said plurality of circumferential segments.

11. The prosthesis of claim 10, wherein selected of said circumferential segments includes a serpentine or zigzag pattern of straight struts interconnected by a plurality of bends.

12. The prosthesis of claim 1, wherein said tubular member comprises a second expandable stent that is self-expanding, balloon expandable or a combination of both.

13. The prosthesis of claim 12, wherein each of said first and said second stents has an inside diameter and an outside diameter and wherein said first stent in a relaxed condition has an outside diameter less than an inside diameter of said second stent in a relaxed condition.

14. The prosthesis of claim 12, wherein said first stent in a relaxed condition has an outside diameter greater than an inside diameter of said second stent in a relaxed condition.

15. The prosthesis of claim 12, wherein said first and said second stents in a relaxed condition have equivalent inside and outside diameters.

16. The prosthesis of claim 1, wherein said tubular member comprises a perforated polymer material.

17. The prosthesis of claim 1, wherein said tubular member is disposed completely over said tissue graft.

18. The prosthesis of claim 1, wherein at least one end of said first stent extends beyond at least one end of said tissue graft.

19. A stent tissue graft prosthesis comprising:
    a first expandable stent having a first distal stent end and a first proximal stent end, a tubular wall and a passage extending longitudinally therethrough,
    a multilayered tissue graft construct having the property of eversion upon placement in a blood vessel if not supported, the multilayered tissue graft construct having a distal construct end and a proximal construct end, a tubular wall and a passage extending longitudinally therethrough and disposed on said first stent, and
    a second expandable stent having a distal second expandable stent end and a proximal second expandable stent end, a tubular wall and a passage extending longitudinally therethrough, said second stent being disposed over and around said construct and said first stent, and retaining said construct disposed on said first stent solely by compressive forces, wherein the compressive forces are provided at least by an outward expansion of the first stent,
    wherein, in a pre-implantation configuration, a most distal end of the first distal stent end is at least coincident with a most distal end of the distal construct end and a most proximal end of the first proximal stent end is at least coincident with a most proximal end of the proximal construct end and where during implantation and post-implantation of the prosthesis, the most distal construct end and the most proximal construct end remain substantially in the pre-implantation configuration such that the construct does not evert or fold into the passage of the first expandable stent, and
    wherein the distal and the proximal second expandable stent ends are substantially coincident with the respective distal and proximal first stent ends.

20. A stent tissue graft prosthesis comprising:
a first expandable stent having a first distal stent end and a first proximal stent end, a tubular wall and a passage extending longitudinally therethrough,
a tissue graft having the property of eversion upon placement in a blood vessel if not supported, the tissue graft having a distal tissue graft end and a proximal tissue graft end and disposed on said first stent, and
a tubular member having a distal tubular member end and a proximal tubular member end, a wall and a passage extending longitudinally therethrough, said tubular member being disposed over said tissue graft and around said first stent and retaining said tissue graft disposed on said first stent solely by compressive forces, wherein the compressive forces are provided at least by an outward expansion of the first stent,
wherein, in a pre-implantation configuration, a most distal end of the first distal stent end extends beyond a most distal end of the distal tissue graft end and a most proximal end of the first proximal stent end extends beyond a most proximal end of the proximal tissue graft end and where during implantation and post-implantation of the prosthesis, the most distal tissue graft end and the most proximal tissue graft end remain substantially in the pre-implantation configuration such that the tissue graft does not evert or fold into the passage of the first expandable stent, and
wherein the distal and the proximal second expandable stent ends are substantially coincident with the respective distal and proximal first stent ends.

21. A stent tissue graft prosthesis comprising:
a first expandable stent having a first distal stent end and a first proximal stent end, a tubular wall and a passage extending longitudinally therethrough,
a multilayered tissue graft construct having the property of eversion upon placement in a blood vessel if not supported, the multilayered tissue graft construct having a distal construct end and a proximal construct end, a tubular wall and a passage extending longitudinally therethrough and disposed on said first stent, and
a second expandable stent having a distal second expandable stent end and a proximal second expandable stent end, a tubular wall and a passage extending longitudinally therethrough, said second stent being disposed over and around said construct and said first stent, and retaining said construct disposed on said first stent solely by compressive forces, wherein the compressive forces are provided at least by an outward expansion of the first stent,
wherein, in a pre-implantation configuration, a most distal end of the first distal stent end extends beyond a most distal end of the distal construct end and a most proximal end of the first proximal stent end extends beyond a most proximal end of the proximal construct end and where during implantation and post-implantation of the prosthesis, the most distal construct end and the most proximal construct end remain substantially in the pre-implantation configuration such that the construct does not evert or fold into the passage of the first expandable stent, and
wherein the distal and the proximal second expandable stent ends are substantially coincident with the respective distal and proximal first stent ends.

* * * * *